United States Patent [19]

Sahm et al.

[11] 4,002,423

[45] Jan. 11, 1977

[54] BENZOFURAN DERIVATIVES PROCESS FOR THEIR PREPARATION AND THEIR USE AS OPTICAL BRIGHTENERS

[75] Inventors: Wilfried Sahm, Kelkheim, Taunus; Erich Schinzel, Hofheim, Taunus; Gunter Rösch, Altenhain, Taunus, all of Germany

[73] Assignee: Hoechst Aktiengesellschaft, Frankfurt am Main, Germany

[22] Filed: Oct. 11, 1974

[21] Appl. No.: 513,997

Related U.S. Application Data

[62] Division of Ser. No. 279,531, Aug. 10, 1972, Pat. No. 3,859,350.

[30] Foreign Application Priority Data

Aug. 13, 1971 Switzerland .................... 11924/71

[52] U.S. Cl. .................... 8/1 W; 8/137; 252/542; 252/558; 260/40 R; 264/78
[51] Int. Cl.² .................... D01F 2/14; D01F 2/16; D06L 3/12
[58] Field of Search .......... 252/301.2 W, 558, 542; 264/78; 8/1 W, 137; 260/40 R, 346.2 R, 240 CA, 240 D, 240 E

[56] References Cited

UNITED STATES PATENTS 3,697,513   10/1972   Siegrist .................... 260/240 R

FOREIGN PATENTS OR APPLICATIONS 7,009,485   12/1970   Netherlands .................... 260/307
1,313,332   4/1973   United Kingdom ............... 260/307

OTHER PUBLICATIONS

Abe et al.: *Nippon Kagaku Zasshi*, vol. 87, pp. 870–876 (1966).
Kobayashi et al.: "Adsorptive Cyclization Reaction", *Tetrahedron Letters*, No. 1, pp. 71–74, 1971.
Toda et al.: *Chemical Abstracts*, vol. 56, col. 2366 (1962).

*Primary Examiner*—Dennis L. Albrecht
*Attorney, Agent, or Firm*—Connolly and Hutz

[57] ABSTRACT

New bisbenzofuranes which are connected by a direct bond or a bridgemember being in conjugation with the double bonds of the furane nuclei are obtained by intra- or intermolecular condensation reactions. The products are useful as optical brighteners, especially for detergents.

8 Claims, No Drawings

BENZOFURAN DERIVATIVES PROCESS FOR THEIR PREPARATION AND THEIR USE AS OPTICAL BRIGHTENERS

This application is a division of application Ser. No. 279,531 filed Aug. 10, 1972 and now U.S. Pat. No. 3,859,350.

The present invention relates to novel benzofurane derivatives, to a process for their preparation and to their use as optical brighteners.

It is already known to prepare 2,5-bis-[benzofuranyl-(2)]-1,4,4-oxidiazoles (German Offenlegungsschrift No. 2,031,774). It is also known that these compounds are useful as optical brighteners for organic materials.

The present invention relates to benzofurane derivatives which are of a slightly yellow color and show in dissolved form a violet blue to greenish blue fluorescence and correspond to the formula (1)

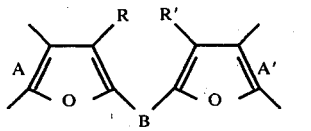

wherein A and A' represent aromatic, mono- or polynuclear ring systems wherein two adjacent carbon atoms are condensed with the furane nucleus in the manner indicated, R and R' represent hydrogen or halogen atoms, lower alkyl groups, phenyl groups which may be substituted by lower alkyl or lower alkoxy groups or halogen atoms as well as carboxy or sulfo groups which acidic groups may be modified, such as lower alkyl ester groups, amide groups, lower monoalkyl amide or lower dialkylamide groups.

B represents a direct bond or a continuously conjugated chain of carbon atoms, which may be completely or partly a constituent of carbocyclic or heterocyclic ring systems and is conjugated with the double bonds of the two furane rings.

Non-chromophoric substituents may be bound to the aromatic ring system A or A', namely alkyl, alkenyl, alkoxy, aryl groups, carboxy or sulfo groups which may optionally be modified, acyl, acylamino or sulfonyl groups as well as halogen atoms. Several of the mentioned groups, which may be identical or different from one another, may also be bound simultaneously to A or A'. A and A' as well as R and R' may be identical or different from one another.

Among the definitions given under A and A' as well as R and R', a carboxy group having modified functions means first the salts of this group formed with colorless cations, alkali metal or ammonium ions being preferred, and furthermore the functional derivatives of a carboxy group, from the carbon atom of which three bonds lad to hetero atoms, especially as in the cyano group, a carboxylic ester group or a carboxylic acid amide group.

Carboxylic acid ester groups are especially those having the general formula $COOR^1$, in which $R^1$ represents a phenyl radical or an optionally branched lower alkyl group, wherein these radicals may contain further substituents such as a preferably low-molecular dialkylamino, trialkyl ammonium or an alkoxy group. A carboxylic acid amide group is especially a group having the formula $CONR^2R^3$, in which the radicals $R^2$ and $R^3$ represent hydrogen atoms or lower, optionally substituted alkyl groups which may form with the nitrogen atom a hydroaromatic radical, especially one of five or six ring members, preferably piperidino, piperazino or morpholino; furthermore acid hydrazides and the analogous thioderivatives.

A sulfo group having modified functions — in analogy to the preceding explanations — represents the salts of this group formed with colorless cations, preferably alkali metal or ammonium ions and furthermore the derivatives, in which the $SO_2$ group is bound to a hetero atom, as in the sulfonic acid ester group which especially means a group of the formula $SO_2OR^1$, wherein $R^1$ has the above meaning, and a sulfonic acid amide group which means a group of the formula $SO_2NR^2R^3$, in which $R^2$ and $R^3$ have the above-mentioned meaning.

An acyl group is especially a group of the formula $COR^4$, wherein $R^4$ represents an optionally substituted, preferably lower alkyl or a phenyl radical.

A sulfonyl radical is especially a radical having the formula $SO_2R^5$, wherein $R^5$ stands for an optionally substituted lower alkyl or a phenyl group; these groups may preferably contain as substituents a lower dialkylamino, trialkyl ammonium, acylamino or sulfo group.

The term "lower," when used in connection with the terms alkyl, alkoxy etc. is intended to cover such aliphatic groups of up to four carbon atoms, i.e. in case of saturated residues from one to four carbon atoms.

Among the compounds of the general formula (1) there are especially interesting those having the general formula (2)

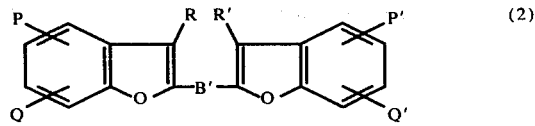

wherein B' means a direct bond or one of the following groups:

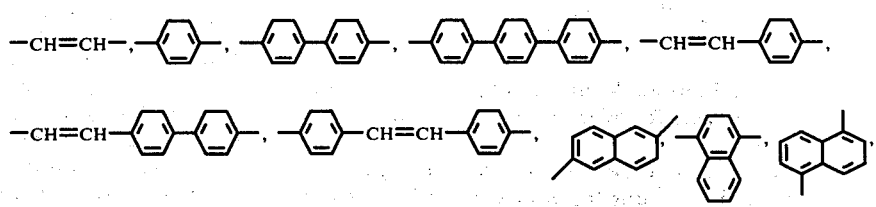

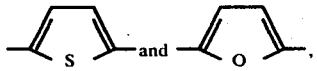

R and R' represent independently from each other hydrogen atoms, lower alkyl, sulfo, sulfonamide, mono and dialkylamide groups having one to four carbon atoms in each alkyl moiety or phenyl, P and Q and P' and Q' represent independently from each other hydrogen or halogen atoms, lower alkyl, lower alkoxy or phenyl, carboxy or sulfo groups being optionally modified as indicated above or P and Q as well as P' and Q' represent together a lower alkylene group or an annellated benzene nucleus.

The compounds according to the invention may be prepared in different ways.

Preferred processes are the processes I to IV referred to below.

In process I compounds of the general formula (3)

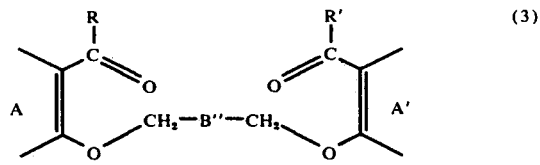

are condensed intramolecularly, with the restriction that B" represents in the process I a diphenyl radical; in the process II compounds of the general formula (4)

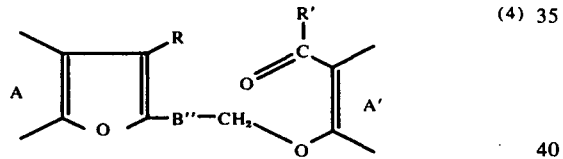

are condensed intramolecularly; in the process III compounds of the general formulae (5) and (6)

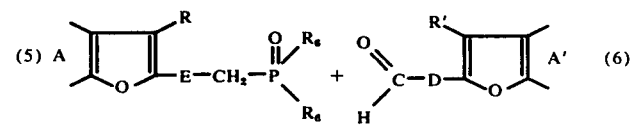

are condensed intramolecularly; and in the process IV compounds of the general formula

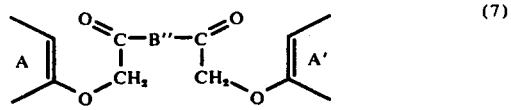

are condensed intramolecularly, whereby in the latter process the radical B" migrates to the 2-position of the furane rings.

The compounds of the general formulae (3) and (4) are prepared by reacting the compounds of the general formula (3a)

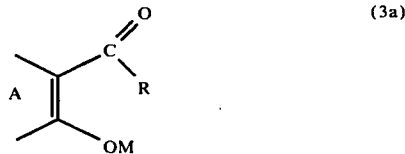

wherein A may be A' and R may be R' and wherein these residues have the above-mentioned meanings and M is an alkaline or alkaline earth metal cation, with compounds of the formula (3b)

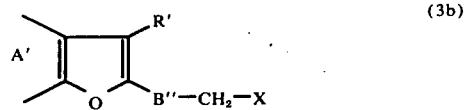

wherein A' may be A and R' may be R and wherein these residues have the above meaning and B" is as defined above and X is the anion of an inorganic acid, preferably of a hydrohalic acid, or by reacting the compounds of the formula (3a) with compounds of the formula (3c)

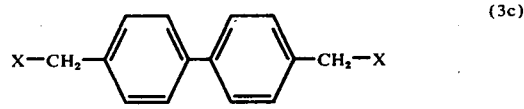

wherein X is as defined above. Suitable starting compounds for these processes are the following ones:

The alkaline or alkaline earth metal salts of the compounds: salicyl aldehyde, 5-chloro-salicyl aldehyde, 3,5-dichlorosalicyl aldehyde, 3-bromosalicyl aldehyde, 4-bromosalicyl aldehyde, 5-bromosalicyl aldehyde, 3,5-dibromosalicyl aldehyde, 3-fluorosalicyl aldehyde, 3-chlorosalicyl aldehyde, 6-methyl-salicyl aldehyde, 5-chloro-6-methyl-salicyl aldehyde, 3-methyl-salicyl aldehyde, 5-methyl-salicyl aldehyde, 4-methyl-salicyl aldehyde, 5-chloro-4-methyl-salicyl aldehyde, 6-ethyl-salicyl aldehyde, 3-ethyl-salicyl aldehyde, 5-ethyl-salicyl aldehyde, 4-ethyl-salicyl aldehyde, 3,5-dimethyl-salicyl aldehyde, 4,5-dimethyl-salicyl aldehyde, 3-phenyl-salicyl aldehyde, 5-phenyl-salicyl aldehyde, 5-fluoro-2-hydroxyacetophenone, 4-methoxy-2-hydroxy-acetophenone, 5-methoxy-2-hydroxy-acetophenone, 3-chloro-2-hydroxy-acetophenone, 5-chloro-2-hydroxy-acetophenone, 3,5-dichloro-2-hydroxy-acetophenone, 5-bromo-2-hydroxy-acetophenone, 3,5-dibromo-2-hydroxy-acetophenone, 3-methyl-2-hydroxy-acetophenone, 5-chloro-3-methyl-2-hydroxyacetophenone, 5-methyl-2-hydroxy-acetophenone, 3-chloro-5-methyl-2-hydroxy-acetophenone, 3-bromo-5-methyl-2-hydroxy-acetophenone, 4-methyl-2-hydroxy-acetophenone, 5-methoxy-2-hydroxy-acetophenone, 5-ethoxy-2-hydroxy-acetophenone, 5-fluoro-2-hydroxy-propiophenone, 5-chloro-2-hydroxy-propiophenone, 3,5-dichloro-2-hydroxy-propiophenone, 5-bromo-2-hydroxypropiophenone, 3,5-dibromo-2-hydroxypropiophenone, 3,5-dichloro-2-hydroxy-benzo-phenone, 3,5-dibromo-2-hydroxy-benzophenone, 5-methyl-2-hydroxy-benzophenone, 3-bromo-5-methyl-2-hydroxy-benzophenone, 2,4,6-trimethyl-2-hydroxy-benzophenone, 2′, 2′,5,6-trimethyl-2-hydroxy-benzophenone, 2-hydroxy-1-naphthaldehyde, 4-chloro-2-hydroxy-1-naphthaldehyde, 1-hydroxy-2-naphthaldehyde, 3-hydroxy-2-naphthaldehyde and methyl-(2-hydroxy-naphthyl-(1))-ketone.

As compounds of the formula (3b) there may be mentioned the following compounds:
2-bromomethyl-benzofurane, 2-bromomethyl-4,5-benzo-benzofurane, 2-bromomethyl-5,6-benzo-benzofurane, 2-chloromethyl-6,7-benzo-benzofurane, 2-bromomethyl-6-bromo-benzofurane, 2-bromomethyl-6-cyano-benzofurane, 2-bromomethyl-6-methoxy-benzofurane, 1-bromomethyl-4-[benzofuryl-(2)]-benzene, 1-bromomethyl-4-[3-bromo-benzofuryl-(2)]-benzene, 1-bromomethyl-4-[3-cyano-benzofuryl-(2)]-benzene, 1-bromomethyl-4-[6-bromo-benzofuryl-(2)]-benzene, 1-bromomethyl-4-]6-cyano-benzofuryl-(2)]-benzene, 1-bromomethyl-4-[6-methoxy-benzofuryl-(2)]-benzene, 1-bromomethyl-4-[benzofuryl-(2)]-naphthalene, 1-bromomethyl-4-[6-cyano-benzofuryl-(2)]-naphthalene, 1-bromomethyl-4-[6-methoxy-benzofuryl-(2)]-naphthalene, 2-bromomethyl-5-[benzofuryl-(2)]-thiophene, 2-bromomethyl-5-[6-cyan-benzofuryl-(2)]-thiophene, 2-bromomethyl-5-[6-methoxy-benzofuryl-(2)]-thiophene, 2-bromomethyl-5-[benzofuryl-(2)]-furane, 2-bromomethyl-5-[5-carbomethoxy-benzofuryl-(2)]-furane, 2-bromomethyl-5-[6-cyano-benzofuryl-(2)]-furane, 2-bromomethyl-5-[6-methoxy-benzofuryl-(2)]-furane.

In the formulae (3), (4), (5), (6) and (7) A, A′, R, R′ and B have the meaning indicated in the general formula (1). B″ means a continuously conjugated chain of carbon atoms, which may be completely or partly a constituent of carbocyclic or heterocyclic ring systems; the conjugated double bonds in B″ are disposed in the way that after the ring closure, they are conjugated with the adjacent double bonds of the furane nuclei.

In the formula (5) R⁶ stands for identical or different alkyl, cycloalkyl, aralkyl or aryl radicals bound, if desired, to the phosphorous atom via an oxygen atom. Since the radicals R⁶ do not appear in the final product, their chemical nature is irrelevant with regard to the product of the process.

In the general formulae (5) and (6) D and E, which may be identical or different, stand for a direct bond or a continuously conjugated chain of carbon atoms, which may be completely or partly a constituent of carbocyclic or heterocyclic ring systems and which are conjugated with the adjacent double bonds of the furane nucleus.

Thus, the compounds of the general formula

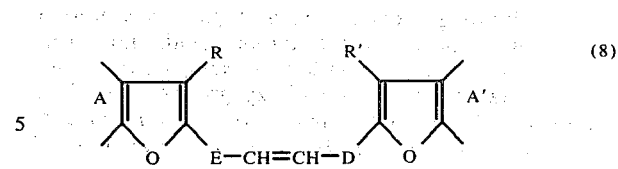

obtained according to the process III contain a middle component —E—CH=CH—D— which has the meaning of B, on the condition that B contains at least one olefinic double bond.

The intramolecular condensations according to the processes I and II are carried out in the presence of strongly polar organic solvents and strongly basic condensation agents.

As examples the following solvents may be used, without any restriction being made: dimethyl formamide, dimethyl acetamide and hexamethyl phosphoric acid triamide. Mixtures of suitable solvents may also be used.

As strongly basic condensation agents there are considered i.a. alkali metals, alkaline earth metals, strongly alkaline compounds thereof and strongly basic aluminum compounds, for example hydroxides, alcoholates, amides or hydrides. The corresponding sodium or potassium compounds are preferably used, for example potassium hydroxide, potassium-tert.butylate or sodium hydroxide. A mixture of different bases may also be used. The basic condensation agents are mostly used in the stoichiometric amount, partly in excess, for example in up to ten times the equivalent amount.

The reaction temperature ranges between about 10° and about 250° C, preferably between about 20° and about 160° C. The reaction is preferably carried out under exclusion of atmospheric oxygen. The ring closure reaction may also be carried out in an alkaline melt, for example in a NaOH—, KOH— or LiOH melt.

The process III is preferably effected in indifferent solvents such as hydrocarbons, as for example toluene or xylene, or in alcohols, such as methanol, ethanol, isopropanol, butanol, glycol, hexanol, cyclohexanol, cyclo-octanol, furthermore in ethers, as for example diisopropyl ether, dioxane or tetrahydrofurane, glycol ethers, for example 2-methoxy-ethanol, furthermore in formamides and N-methyl-pyrrolidone. Dipolar organic solvents such as dimethyl formamide and dimethyl sulfoxide are particularly suitable.

As condensation agents there are considered strongly basic compounds, as for example alkali or alkaline earth metal hydroxides, alkali or alkaline earth alcoholates, alkali or alkaline earth amides, preferably potassium hydroxide, sodium hydroxide, potassium-tert.-butylate or sodium methylate, furthermore the alkali compounds of dimethyl sulfoxide and alkali hydrides.

Depending on the nature of the starting materials, the reaction temperature ranges between about 0° and about 100° C, preferably between about 10° C and about 80° C.

The process IV is preferably carried out in the presence of acidic condensation agents, preferably polyphosphoric acid. The reaction temperature — depending on the nature of the starting materials — ranges between about 50° C and about 230° C, preferably between about 80° C and about 180° C.

The reaction products of the preceding processes may be subjected — of course — to further modifications already known, as for example to sulfonations with sulfonating agents, such as $H_2SO_4$, mixtures of $H_2SO_4$ and $SO_3$ or chloro-sulfonic acid, moreover, modifications which — starting for example from molecules containing sulfo or carboxy groups — lead to compounds having functionally modified sulfo or carboxy groups as defined above or the conversions of such groups into other groups of this type or into the free acids.

The use of the compounds described by the general formulae (3), (4), (5), (6) and (7) together with the radicals A, A', B'', R, R', R⁶, E and D defined above allows to prepare for example the following compounds:

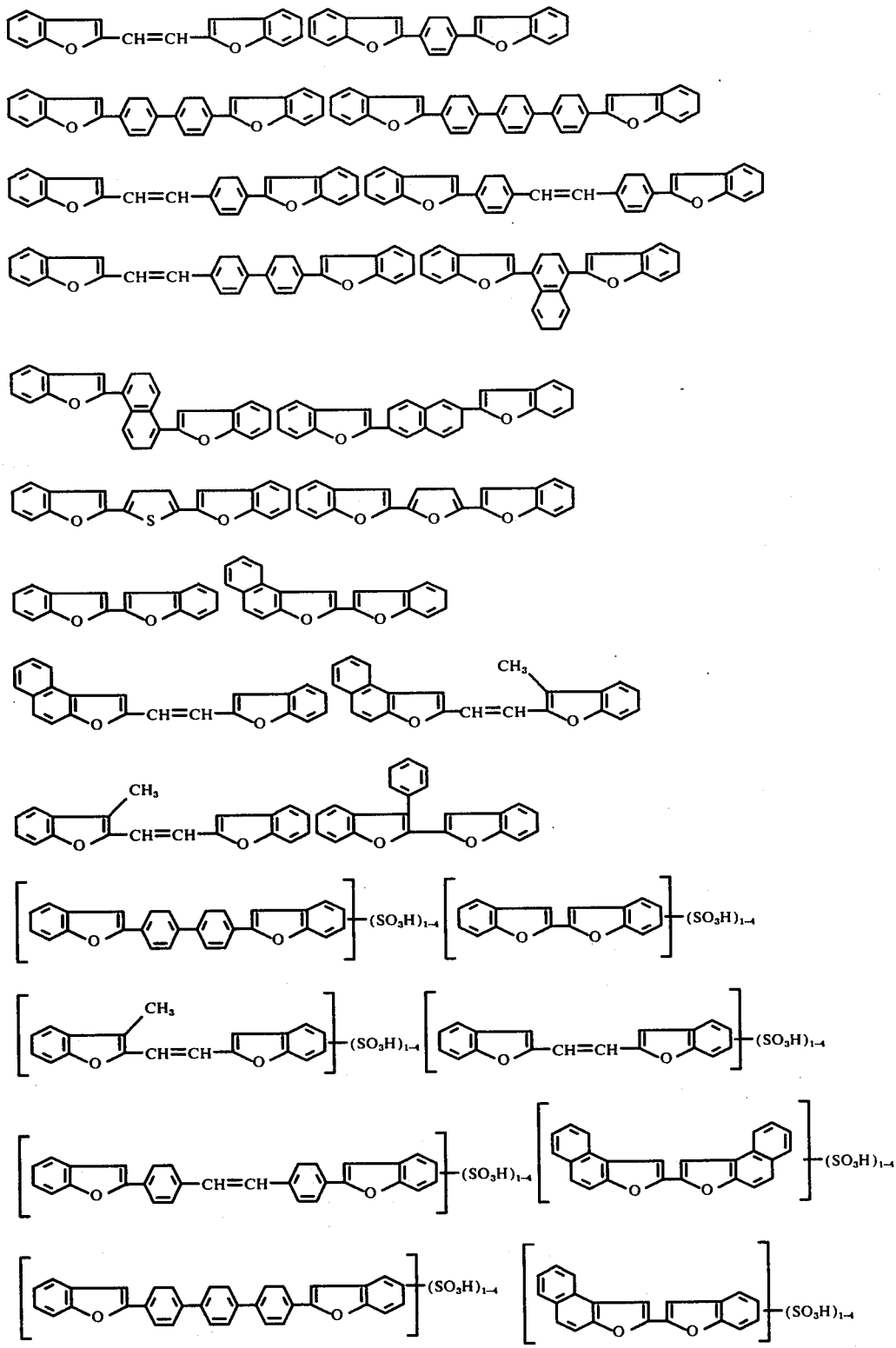

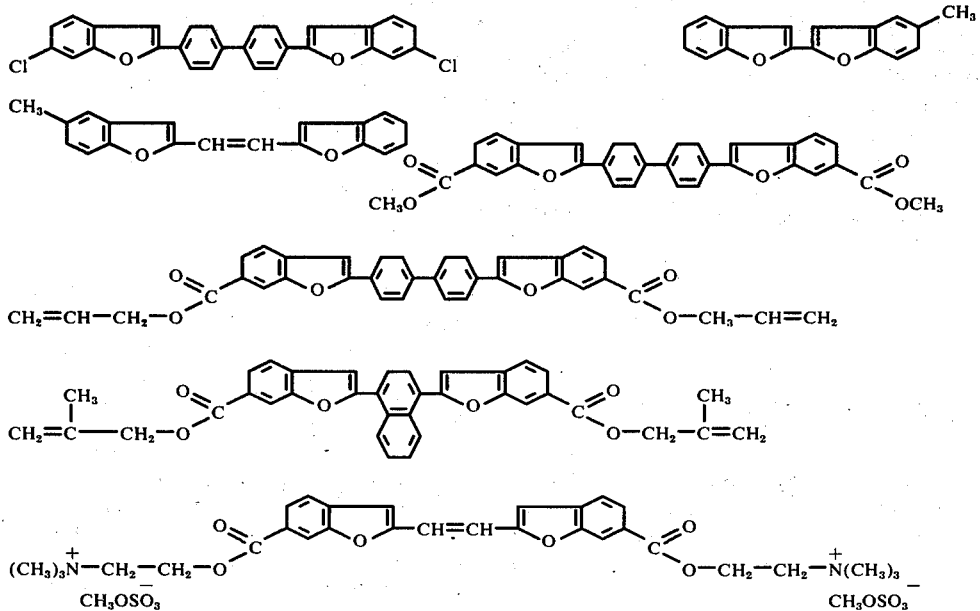

On account of their fluorescent capacity the new compounds according to the invention have a large field of application. They serve above all for the optical brightening of different natural and synthetic organic materials, which also include organic materials which may be used for finishing mineral materials, for example inorganic pigments.

The substrates to be brightened are for example the following materials: lacquers, synthetic fibres such as for example consisting of acetyl cellulose, polyesters, polyolefines, polyvinyl chloride, polyvinylidene chloride or polyacrylo-nitrile as well as foils, films, ribbons or shaped articles made of such materials.

The water-insoluble compounds according to the invention may be used in dissolved form in organic solvents or in an aqueous dispersion, preferably by means of a dispersing agent. There are considered for example as dispersing agents: soaps, polyglycol ether deriving from fatty alcohols, fatty amines or alkyl phenols, cellulose sulfite waste liquors or condensation products of optionally alkylated naphthalene sulfonic acids with formaldehyde.

The water-soluble anionic compounds according to the invention are particularly suitable for the optical brightening of native and regenerated cellulose fibres and of wool and synthetic polyamide fibres.

The compounds containing sulfonic acid groups are especially characterized by an excellent affinity towards cotton and to polyamide fibres. Especially valuable are the very brilliant brightenings in the crease resistant finish of cotton, the excellent fastness to light, the fastness to light when wet and resistance to acids as well as the resistance to chlorite, which is particularly important for the brightening of mixed fabrics which need an additional chlorite bleaching.

The water-soluble cationic compounds according to the invention are particularly suitable for the optical brightening of mixed polymers of acrylonitrile, especially the commercial copolymers having a contents of at least 85% of acrylonitrile.

Benzofuranes of the general formula (1) may also be added to laundry detergents. The latter ones may contain the usual fillers and auxiliaries such as alkali silicates, alkali polyphosphates and alkali polymethaphosphates, alkali borates, alkali salts of the carboxy-methyl cellulose, foam stabilizers, as for example alkanol amides of higher fatty acids or complex formers such as soluble salts of the ethylene-diamine tetraacetic acid or diethylene-triamine-penta-acetic acid as well as chemical bleaching agents, as for example perborates or percarbonates. Very good results are obtained in detergents containing perborate in the presence of perborate activators. The disinfectants usually used in detergents do not adversely affect the brightening effects of the compounds according to the invention.

The fibre material is brightened with the aqueous or, if desired, organic brightening liquor either by the exhaustion process at temperatures reaching preferably from about 20° to about 150° C or under thermosol conditions; by this process the textile material is impregnated with the brightening solution or dispersion and squeezed between rollers to a content of residual moisture of about 50 to about 120%. The textile material is then subjected to a heat treatment for about 10 to about 300 seconds, preferably to dry heat at about 120° to about 240° C. This thermosol process may be combined with other finishing operations, for example finishing with synthetic resins for easy care.

Furthermore, the compounds according to the invention may be added to high-molecular organic materials before or during their shaping. Thus, they may be added to the molding materials in the preparation of films, foils, ribbons or shaped articles or be dissolved in the spinning mass before the spinning process. Suitable compounds may also be added to the low-molecular-weight starting materials before polycondensation or polymerization, as in the case of polyamide-6,polyamide-6, 6 or linear esters of the polyethylene glycol terephthalate type.

Compounds according to the invention substituted by one or preferably two carboxy or carbo-alkoxy groups, may be bound to linear polyester molecules and synthetic polyamides by an ester or amide bond, if they are added to these materials or preferably to their starting compounds under suitable conditions. The brighteners linked by this way to the substrate by a chemical bond, are characterized by an extremely high fastness to sublimation and to solvents.

Olefinically unsaturated compounds according to the invention which contain besides the fluorescent system one olefinic double bond capable of being polymerized, may be used for preparing fluorescent polymers or polymer mixtures, by polymerizing them as such or in mixture with other monomer or polymer vinyl compounds, whereby the fluorescent system is maintained. These fluorescent polymers may be subsequently mixed with not fluorescent polymers. Polymers optically brightened in this manner are characterized by a high degree of whiteness. Furthermore, the chemical bond of the brightening molecules with the polymers insures a high fastness to sublimation and to solvents.

The amount of the compounds to be used according to the invention having the general formula (1), calculated on the material to be optionally brightened, may vary within wide limits, according to the field of application and to the effect desired. It may be easily determined by tests and generally ranges between about 0.01 and about 2%.

The following Examples illustrate the invention.

EXAMPLE 1

21.1 g of 4,4'-bis-(o-formyl-phenoxy)-dibenzyl (melting point: 187° C) were heated in 250 ml of dimethyl formamide (in the following: DMF) with 22.4 g of potassium-tert.-butylate for 6 hours under $N_2$ to the boil. The mixture was cooled, the precipitate formed was suction-filtered, washed with methanol and dried in vacuo at 60° C. Thereby 9.2 g of the crude product having the formula

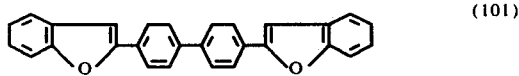
(101)

were obtained. It was recrystallized from 500 ml of benzoic acid methyl ester under addition of charcoal. The crystalline product purified had a slightly yellow color and melted above 300° C.

| $C_{28}H_{18}O_2$ | calc: | C 87.9 | H 4.79 |
|---|---|---|---|
| (386.45) | found: | C 87.5 | H 4.80 |
| $\lambda$ max (absorption/DMF) = 351 nm, $\epsilon$ = 7.06 · $10^4$ | | | |

EXAMPLE 2

10 g of the compound (101) were heated for 7 hours to 60° C in 200 ml of concentrated sulfuric acid. Then the mixture was cooled and poured onto 100 ml of ice water. By neutralizing with sodium hydroxide solution and subsequent salting out with sodium chloride, 40 g of a mixture consisting of sodium chloride, and the sodium salts of the sulfonation product (102)

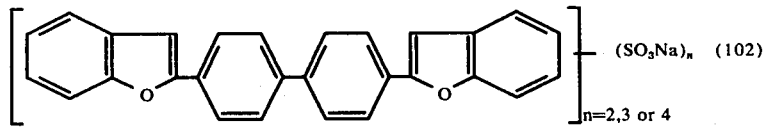
(102)

were obtained. The salt was dried in vacuo at 60° C. The slightly yellow substance mixture was easily soluble in water, bases and acids having an intense blue fluorescence.

$\lambda$ max (absorption/$H_2O$) = 354 nm, $\epsilon$ = 6.63·$10^4$ average molecular weight found: 745; calculated for n = 3: 693; for $n$ = 4: 795.

The mixture can be split into its components in known manner, such as by chromatography or fractionated crystallization.

EXAMPLE 3

26.8 g of benzofuryl-(2)-methyl-diethyl phosphonate were dissolved together with 14.6 g of benzofurane-2-aldehyde in 150 ml of DMF. Under cooling with ice, 12.5 g of sodium hydroxide (powdered, of about 80% strength) were added. The mixture was allowed to react while stirring for one hour at room temperature. Then the mixture was introduced while stirring into 500 ml of ice water, adjusted to neutral with hydrochloric acid and the precipitate was suction-filtered. After drying, the whole was crystallized twice from 400 ml of n-butanol in each case under addition of charcoal. Thereby, 12 g of slightly yellow brilliant lamellas of the formula

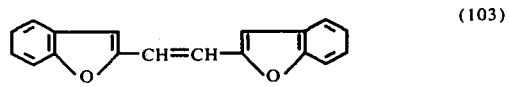
(103)

were obtained having a melting point of 185°–186° C.

The sulfonic acid derivative (104) may be prepared from the compound (103) in an analogous manner as indicated in Example 2.

EXAMPLE 4

13.4 g of benzofuryl-(2)-methyl-diethyl phosphonate were reacted with 8 g of 3-methyl-benzofurane-2-aldehyde and 6.2 g of sodium hydroxide in 100 ml of DMF in analogy to Example 3. After working up in the manner described, 7.7 g of yellow crystals of the formula

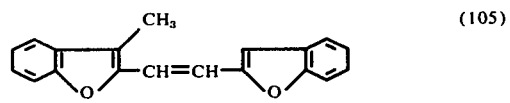
(105)

were obtained, having a melting point of 97°–98° C.

The compounds (106), (107), (108) and (109) of the following formulae are obtained in analogous way:

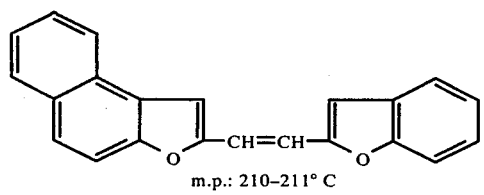

(106)

m.p.: 210–211° C

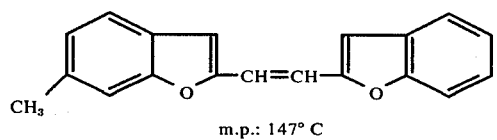

(107)

m.p.: 147° C

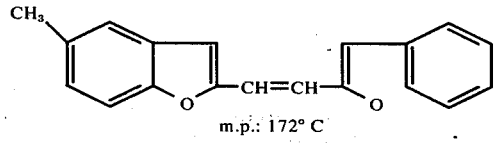

(108)

m.p.: 172° C

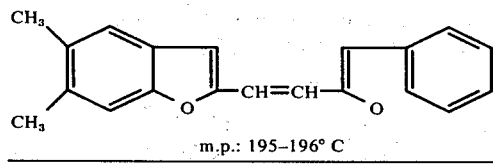

(109)

m.p.: 195–196° C

EXAMPLE 5

21.1 g of 2-bromomethyl-benzofurane were heated to the boil together with 14.8 g of salicyl-aldehyde-sodium for 45 minutes in DMF. Then the mixture was cooled and introduced while stirring into a mixture of 250 ml of 1N hydrochloric acid and 250 ml of water. The precipitate was suction-filtered, washed neutral with water and dried in vacuo at 60° C.

Thus, 22.5 g of the compound

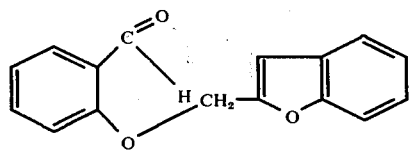

(110)

were obtained having a melting point of 62°–63° C.

20 g of the compound (107) were treated in 100 ml of boiling DMF for 30 minutes with 8 g of potassium-tert.-butylate. While cooling, the compound

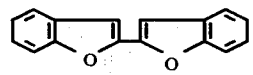

(111)

was crystallized in the form of slightly yellow needles. It was suction-filtered, washed with ethanol and dried in vacuo. Yield: 15.3 g, melting point: 197°–198° C.

EXAMPLE 6

10 g of the compound (108) were heated for 2 hours to 60° C in 30 ml of concentrated $H_2SO_4$ in analogy to Example 2. According to the method described, 35 g of a mixture of sodium chloride, sodium sulfate and the sodium salt of the compound

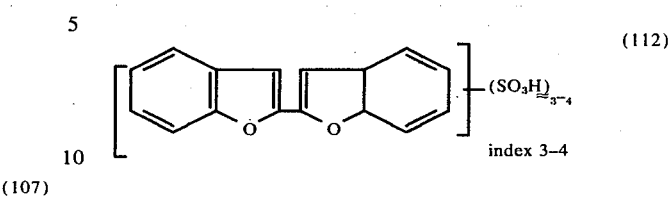

(112)

index 3–4 were obtained. The salt was dried at 60° C in vacuo. The slightly yellow substance mixture was easily soluble in water, bases and acids having a strong fluorescence.

λ max (absorption/ 1 N $H_2SO_4$) = 353 nm.

EXAMPLE 7

When proceeding according to Example 5 but using instead of the salicyl-aldehyde sodium the sodium salt of the 2-naphthol-1-aldehyde and the compound

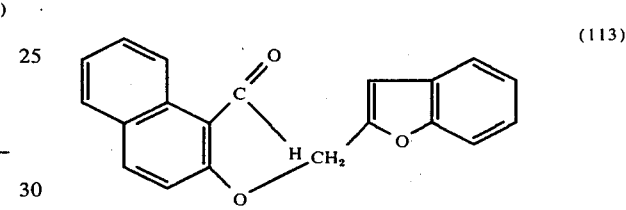

(113)

being isolated intermediately, the compound

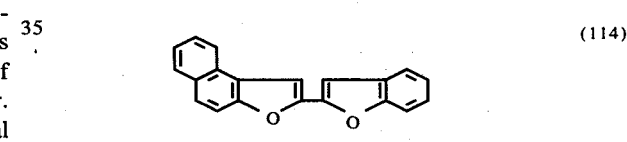

(114)

having a melting point of 171° C was obtained.

From the compound (114) the corresponding sulfo derivative can be prepared by sulfonation in analogy to Example 6.

EXAMPLE 8

If the process was carried out as described in the Examples 5 and 7 and the compound

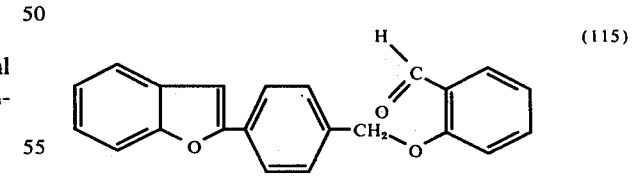

(115)

melting point: 108–110° C was condensed, the compound

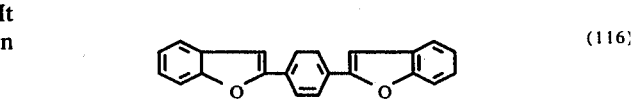

(116)

was obtained, which could be easily converted into the compounds (117) and (118)

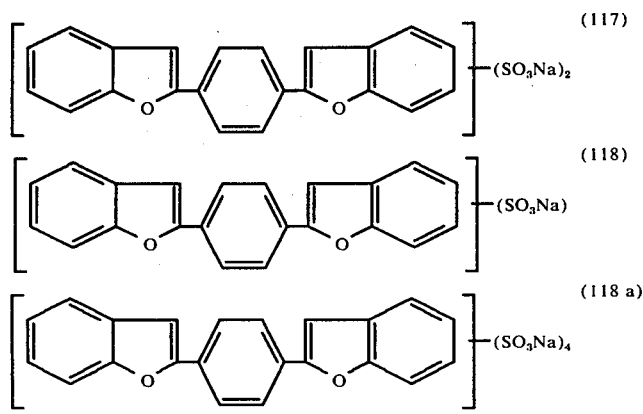

by sulfonating with concentrated $H_2SO_4$.

EXAMPLE 9

At an interior temperature of a maximum of 50° C, a solution of 16.8 g of the compound

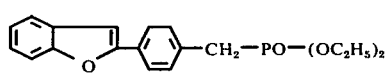 (119)

and 7.4 g of benzofurane-2-aldehyde in 200 ml of DMF were added dropwise to a suspension of 44 g of pulverized sodium hydroxide of about 90% strength in DMF. After allowing a reaction for 60 minutes, the mixture was cooled to +5° C and the resulting precipitate was suction-filtered. The filter residue was washed neutral with water, then with methanol and dried in vacuo at 60° C. Thereby, 9.1 g of a crude product of the compound of the formula (120)

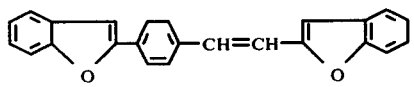 (120)

having a melting point of 290° C (from DMF) were obtained.

The compounds (121) to (124) having the following formulae were obtained in analogous way:

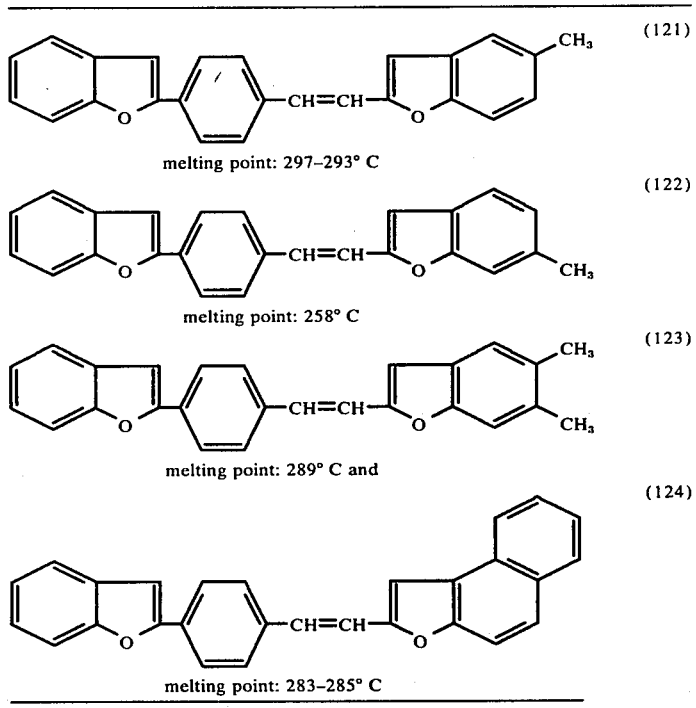

By reacting (119) with 2-(p-formyl-phenyl)-benzofurane under the afore-mentioned conditions, the compound of the formula (125)

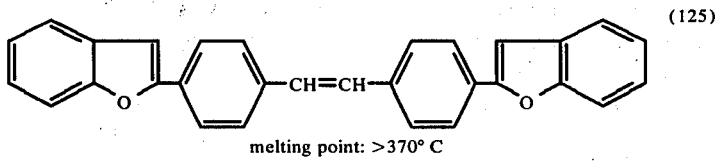

(125)

melting point: >370° C was obtained.

| Analysis: | $C_{30}H_{20}O_2$ | Calc: | C 87.4 | H 4.88 |
|---|---|---|---|---|
| | (412.46) | Found: | C 87.6 | H 4.94 |
| $\lambda$ max (absorption/DMF) = 384 nm, = 8.9 · 10⁴ | | | | |

EXAMPLE 10

A cotton fabric, which was previously bleached with hydrogen peroxide in known manner and then dried, was impregnated with a solution containing 2 g/l of the optical brighteners of the formula (102), 250 g of a dimethylol-dihydroxy-ethylene-urea resin and 120 ml of hydrochloric acid. The cotton fabric was squeezed off between rollers. The contents of residual moisture amounted to 60%. The fabric was wound up onto rollers and stored for 18 hours at room temperature. After washing and drying, the material showed an excellent degree of whiteness (according to Berger, Die Farbe 8 (1959) 187 ff, $W = \overline{Y} + 3(\overline{Z} + \overline{X})$) of 181.3% compared with 74.8% of the untreated goods).

EXAMPLE 11

A mixed fabric consisting of equal parts of cotton and polyethylene-glycol-terephthalate fibres, which was singed and desized in the usual manner, was impregnated with a solution containing 3 g/l of the optical brighteners of the formula (102) and 15 g/l of sodium chlorite. By adding 3 g/l of monoammonium phosphate, the sodium chlorite was activated in known manner. The cotton fabric thus-impregnated was squeezed off between rollers and adjusted to a contents of moisture of 75%. The fabric was steamed for 1 minute with saturated steam of 100° C and stored for another 45 minutes in a steam atmosphere of 98° C. Then it was washed as usual, rinsed and dried. The fabric showed the excellent degree of whiteness of 182.2% as compared with 83.4% of the good bleached in the same way, but treated without any optical brighteners.

The compounds (117), (118) or (118a) or a mixture of these compounds may be used in the same way.

EXAMPLE 12

A rashel lace consisting of equal parts of polyamide 6 and regenerated cellulose was treated in a bath in a goods-to-liquor ratio of 1:12, which contained 0.5 g/l of the optical brighteners of the formula (102), 1.5 g/l of sodium chlorite and 0.4 g/l of a wetting agent on the basis of an oxethylated fatty alcohol with an alkyl radical of 8 carbon atoms (on an average) and 12 ethyleneglycol-ether units (on an average) in the molecule.

The affinity of the optical brightener towards the cotton was increased by adding 5 g/l of sodium sulfate. For activating the sodium chlorite, the bath was adjusted to pH 4 with formic acid.

At 20° C the good was introduced into the bath and heated to 50° C. This temperature was maintained for 60 minutes and then raised to 80° C. After a ten minutes treatment, the bath being constantly agitated, it was cooled and the good rinsed thoroughly. After drying both fibre portions were subjected to a uniform optical brightening, and they showed a degree of whiteness of 167.4% as compared with the good bleached without adding a brightener having a degree of whiteness of 78.3%.

Excellent degrees of whiteness were also achieved with the compounds (117), (118 and (118a) or a mixture of these compounds.

EXAMPLE 13

A cotton fabric was treated in a wash liquor having a goods-to-liquor-ratio of 1:25, which contained 6 g/l of a detergent having the following composition:

9.8% of isotridecanol — polyglycol ether with 8 mols of ethylene oxide per mol of isotridecanol.
30% of sodium tripolyphosphate
15% of tetrasodium pyrophosphate
5% of sodium metasilicate
2% of carboxymethyl cellulose
38% of sodium sulfate
0.05% of the optical brighteners (102)

as well as 0.1 g/l of active chlorine from sodium hypochlorite.

The fabric was washed at 40° C for 10 minutes, rinsed and dried. This treatment was repeated up to five times. The fabric showed an excellent degree of whiteness and a considerable increase as compared with the unwashed material.

| | Degree of whiteness |
|---|---|
| Untreated good | 74.8 |
| washed once | 114.2 |
| washed five times | 133.6 |

EXAMPLE 14

A fabric made of polyethylene glycol terephthalate was impregnated with a bath, which contained in dispersed form 0.8 g/l of the optical brightener of the formula (101). The textile material thus treated was squeezed off between rollers until it contained only 60% of its dry weight of liquid and then subjected to a treatment with air heated to 190° C. After the treatment, the fabric showed the excellent degree of whiteness of 155.7%, compared to 78.8% of the not treated material.

Good results were also obtained with the compounds (116), (120), (121), (122) and (123).

EXAMPLE 15

1000 Parts by weight of ε-caprolactame were melted at about 100° C in a glass apparatus continuously maintained under nitrogen provided with a steel stirrer and a descending cooler. Calculated on the amount of caprolactame used, 0.08% by weight of the compound (101) and 0.34% by weight of a 12% aqueous $TiO_2$-suspension were added. The mixture was heated while stirring for one hour to 175°–180° C. After one hour the temperature was further increased to 275° C and the whole was stirred for about 5 hours at this temperature. At the end of the reaction time, a stronger stream of nitrogen was introduced, in order to distill off the lactame in excess. The polyamide melt thus prepared was passed through a slot die having the form of a ribbon, quenched in water, chipped and dried.

A fabric obtained from this polycondensate by spinning and knitting showed a much better degree of whiteness of a good fastness to light than a fabric prepared in the same manner, but without addition of a brightener.

EXAMPLE 16

In a glass apparatus provided with a stirrer, a gas inlet pipe, a vacuum device and a descending cooler, 400 g of dimethyl terephthalate, 310 g of ethylene glycol and 0.5 g of antimony oxide were heated under nitrogen to an external temperature of about 200° C. This temperature was maintained for 3 hours, while methanol was slowly distilled off. Then 0.4 g of the compound (125) and 20 g of a 20% $TiO_2$ suspension in ethylene glycol were added, the external temperature was increased to 285° C and while slowly reducing the pressure to 0.2 mm of mercury, the ethylene glycol was distilled off in the course of three hours. The bloc of optically brightened polyester material obtained by this way after cooling, was comminuted, granulated and spun to threads in usual manner or pressed to foils.

The threads of foils thus obtained had a brilliant appearance and good fastness to light.

EXAMPLE 17

10 kg of knitted fabric of polyamide 6 were treated with a bath which contained 0.3 g/l of the brighteners of the formula (102) and 2 g/l of a 50% sodium chlorite. The bath was adjusted to pH 3.5 with formic acid and heated to 80° C within 20 minutes. Then the material was treated for 30 minutes at this temperature, rinsed as usual and dried. The polyamide knitted fabric had an excellent degree of whiteness of 195% (according to Berger) exceeding, thus, by a 15% the degree of whiteness obtained with the most suitable known optical brighteners under the same conditions. The degree of whiteness of the not treated material was 76%.

EXAMPLE 18

A fabric of polyamide 6 was impregnated with a solution which contained per liter
3 g/l of the compounds of the formula (102)
15 g/l of polyethylene glycol of a molecular weight of 400 (on an average).
2 ml of formic acid
The fabric was squeezed off between rollers to reach a content of moisture of 70% and then subjected to a thermosol process at 190° C for 20 seconds. Then the fabric showed a degree of whiteness of 147% (according to Berger), which exceeded by 72% that of the untreated product.

Similar results were achieved when using the compounds (117), (118) and (118a) or a mixture of these compounds.

EXAMPLE 19

A cotton fabric pre-treated in usual manner in an alkaline medium was impregnated with a solution which contained per liter
25 g/l of hydrogen peroxide (of 35% by weight)
6 g/l of sodium bicarbonate
2 g/l of sodium carbonate
9 g/l of monosodium phosphate
and
2 g/l of the compounds of the formula (102).

The fabric was squeezed off between rollers to a contents of moisture of 100% and treated for one hour with saturated steam of 100° C. Then the fabric was rinsed hot and cold twice for 5 minutes each and dried. The degree of whiteness was 173% (according to Berger).

EXAMPLE 20

A cotton fabric pretreated according to Example 11, but without optical brighteners, was impregnated with a solution, which contained per liter:
100 g/l of dihydroxy-ethylene urea
15 g/l of magnesium chloride
2 g/l of the optical brighteners of the formula (102).

The fabric thus impregnated was previously dried at 110° C and condensed for 3 minutes at 150° C in dry heat. The fabric did not only show an excellent crease resistant effect (crease angle of 223°), but a degree of whiteness of 173% (according to Berger).

EXAMPLE 21

A bleached cotton fabric boiled in an alkaline medium was impregnated with a solution, which contained
150 g/l of propylene urea
20 g/l of magnesium chloride
1 g/l of the optical brighteners of the formula (102).

The fabric was squeezed off between rollers to a contents of moisture of 100% and then dried at 120° C. Subsequently it was condensed for 10 minutes at 170° C under permanent press conditions. It showed a degree of whiteness of 147% (according to Berger), being, thus, superior to the optical brighteners hitherto used under these conditions.

Instead of the optical brighteners of the formula (102) mentioned in Examples 10 to 13 and 17 to 21 likewise the isolated components can be used.

The following compounds may be used in analogous way, as described in the Examples 10 to 21, which can be synthesized in analogy to the afore-mentioned methods of preparation or prepared from such products by further chemical conversions according to known processes (Table 1):

| No. | Composition | λ max [nm] (Absorption/DMF) | Melting point °C |
|---|---|---|---|
| 126 | | 347 | 241 |
| 127 | | 354 | > 350 |
| 128 | | 350 | 240–242 |
| 129 | | 354 | > 350 |
| 130 | | 356 | 270–272 |
| 131 | | 354 | > 350 |
| 132 | | 350 | 297–301 |
| 133 | | 354 | > 350 |
| 134 | | 352 | 250–251 |
| 135 | | 360 | > 350 |
| 136 | | 357 | 268–270 |
| 137 | | 376 | > 350 |

-continued

| No. | Composition | λ max [nm] (Absorption/DMF) | Melting point °C |
|---|---|---|---|
| 138 | | 363 | 289–290 |
| 139 | | 353 | 145 |
| 140 | | 352 | > 350 |
| 141 | | 378 | 182 |
| 142 | | 380 | 229 |
| 143 | | 381 | 190 |
| 144 | | 383 | 203 |
| 145 | | 393 | 210 – 213 |
| 146 | | 363 | |
| 147 | | 354 | |
| 148 | | 372 | |

-continued

| No. | Composition | λ max [nm] (Absorption/DMF) | Melting point °C |
|---|---|---|---|
| 149 | | 385 | |
| 150 | | 356 | |
| 151 | | 381 | |
| 152 | | 391 | |
| 153 | | 362 | |
| 154 | | 364 | |
| 155 | | 349 | |
| 156 | | 351 | |
| 157 | | 359 | |
| 158 | | 381 | |
| 159 | | 356 | |
| 160 | | 350 | |

We claim:

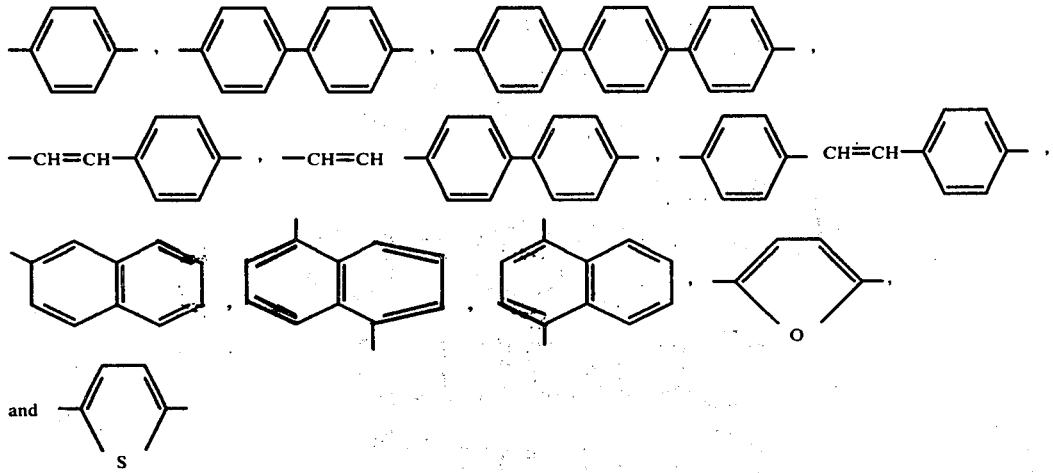

in which B' is a direct bond, vinylene or a bivalent radical being in conjugation with the adjacent double bonds of the furane nuclei selected from the group consisting of phenylene, biphenylene, terphenylene, styryl, biphenylylethylene, stilbylene, naphthylene, furanylene and thienylene;

R and R' which are identical or different, are hydrogen, halogen, lower alkyl, phenyl, or SO₃M;

M is a colorless cation;

P, Q, P' and Q', which are identical or different, are hydrogen, halogen, lower alkyl, lower alkoxy, phenyl, COOM, SO₃M, lower carboalkoxy, sulfonic acid lower alkyl ester, cyano, or a group of the formulae

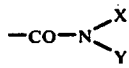 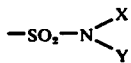

in which X and Y, which are identical or different, are hydrogen, or lower alkyl, or stand together with the nitrogen for piperidyl, morpholyl or piperazyl, and P and Q together or P' and Q' together are the same or different bivalent radicals selected from the group consisting of lower alkylene and an anellated benzene nucleus; and m is a number from 0 to 4.

2. A process as defined in claim 1, wherein B' is a direct bond or a bivalent radical selected from the group consisting of —CH=CH—, R and R', which are identical or different, are hydrogen, chlorine, bromine, lower alkyl or SO₃M;

M is hydrogen, alkali metal, ammonium, quaternary ammonium or an equivalent of an alkaline earth metal, zinc or aluminum, P, Q, P' and Q', which are the same or different, are hydrogen, chlorine, bromine, lower alkyl, lower alkoxy, COOM, SO₃M, lower carbalkoxy or cyano, or P and Q together and/or P' and Q' together are lower alkylene or an annellated benzene nucleus; and m is a number of 0 to 4.

3. A processs as defined in claim 1, wherein said material is a fibre material.

4. A process as defined in claim 3, wherein adding is effected by brightening said material with a brightening liquor according to the exhaustion process or by impregnation.

5. A process as defined in claim 1, wherein said material is a high-molecular weight organic material.

6. A process as defined in claim 5, wherein adding is effected before or during shaping said material.

7. A process as defined in claim 5, wherein said compound is added to the low molecular weight starting materials before polycondensation or polymerization.

8. A process as defined in claim 1, wherein said compound is water-insoluble and added in dissolved form in organic solvents or in an aqueous dispersion.

* * * * *